United States Patent
Brock-Fisher et al.

(10) Patent No.: US 6,997,875 B2
(45) Date of Patent: *Feb. 14, 2006

(54) ACOUSTIC BORDER DETECTION USING POWER MODULATION

(75) Inventors: George A Brock-Fisher, Andover, MA (US); David M Prater, Andover, MA (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 267 days.

This patent is subject to a terminal disclaimer.

(21) Appl. No.: 10/117,809

(22) Filed: Apr. 8, 2002

(65) Prior Publication Data

US 2002/0111553 A1    Aug. 15, 2002

Related U.S. Application Data

(62) Division of application No. 09/502,383, filed on Feb. 11, 2000, now Pat. No. 6,398,732.

(51) Int. Cl.
*A61B 8/00* (2006.01)
*A61B 8/12* (2006.01)
*A61B 8/14* (2006.01)

(52) U.S. Cl. ..................... 600/443; 600/458

(58) Field of Classification Search ............... 600/437, 600/440–441, 443, 447, 454–456, 458; 128/916
See application file for complete search history.

(56) References Cited

U.S. PATENT DOCUMENTS

| | | | | |
|---|---|---|---|---|
| 5,195,521 A | * | 3/1993 | Melton et al. .......... | 600/438 |
| 5,309,914 A | * | 5/1994 | Iinuma ................... | 600/443 |
| 5,568,811 A | * | 10/1996 | Olstad .................... | 600/443 |
| 5,860,931 A | * | 1/1999 | Chandler ................ | 600/458 |
| 6,106,456 A | * | 8/2000 | Storz ..................... | 600/102 |
| 6,217,520 B1 | * | 4/2001 | He et al. ................ | 600/467 |
| 6,398,732 B1 | * | 6/2002 | Brock-Fisher et al. ... | 600/443 |

* cited by examiner

*Primary Examiner*—Francis J. Jaworski

(57) ABSTRACT

The method of the invention controls an ultrasound system to identify a boundary between a tissue region and a blood-filled region that lies within an ROI. The method initially administers a contrast agent to the region of interest and then transmits first and second ultrasound beams at a different power levels into the ROI. Signal returns from the first and second beams are processed to derive first and second digital values, respectively. It has been determined that, under certain circumstances, a phase change of echo returns occurs at the boundary between tissue and blood-containing contrast agent. Detection of the phase change enables precise identification of the boundary, based upon the time segment in which the phase change is detected. Accordingly, time segment values of the first and second stored digital values are then phase-compared to enable determination of a boundary location between the tissue region and the blood-filled region by detection of the phase change.

6 Claims, 4 Drawing Sheets

ACOUSTIC BORDER DETECTION USING POWER MODULATION

CROSS REFERENCE TO RELATED APPLICATIONS

This is a divisional of application Ser. No. 09/502,383, filed Feb. 11, 2000 now U.S. Pat. No. 6,398,732.

FIELD OF THE INVENTION

This invention relates to ultrasound imaging systems and, more particularly, to a method for detecting the location of boundaries between tissue regions and blood-filled regions within an area of anatomy being imaged.

BACKGROUND OF THE INVENTION

In the presentation of ultrasound images of anatomical features, there is a continuing need to improve the ability to precisely identify tissue/blood boundaries. The availability of images that precisely identify such boundaries enable an examining physician to better discern physical abnormalities. Recently, to improve the contrast between blood-filled regions and tissue regions, ultrasound contrast agents have been used. Such contrast agents are substances which strongly interact with ultrasonic waves, returning echoes which may be clearly distinguished from those returned by both blood and tissue.

Certain contrast agents consist of microbubbles which present a significant acoustic impedance mismatch and a non-linear behavior in certain acoustic fields. Such non-linear behavior is readily detectable through special ultrasonic processing. One type of microbubble contrast agent comprises microbubbles of an inert gas that are coated with a thin biodegradable coating or shell. Such microbubbles are infused into the body and survive passage through the pulmonary system and circulate throughout the vascular system.

The non-linear response of microbubble contrast agents, as contrasted to a relatively linear response from tissue is illustrated in FIG. 1. There, the return from a contrast agent with increasing levels of acoustic transmit power is plotted versus echo magnitude. As can there be seen, the contrast agent echo response exhibits an exponential relationship whereas the response from tissue is approximately linear. Accordingly, at higher acoustic transmit power levels, the contrast agent echo response exhibits a larger difference from the tissue echo response than at lower acoustic transmit power levels.

U.S. Pat. No. 5,577,505 to Brock-Fisher et al., assigned to the same assignee as this Application, describes a method for enhancing the detection of echo returns from microbubbles in circulation relative to tissue. Brock-Fisher et al. achieve increased sensitivity to non-linear responses from the microbubbles by transmitting a first ultrasound signal at a first power level into a region of interest (ROI) to be imaged. The echo responses gathered from that ultrasound signal are stored, and a second ultrasound signal is applied, at a second power level and the ultrasound echo responses stored.

The ultrasound responses are gain compensated and further processed to subtract one from the other so as to remove most of the linear response values from the exponential echo response signal. What remains corresponds to the exponential response portion of the microbubble contrast agent backscatter. The determined difference values are color-coded and added back into the original image in the spatial areas from which the echo signals were generated, enabling better identification of the blood-filled regions carrying the contrast agent.

Notwithstanding the ability to better image the contrast agent in areas of blood circulation, there still is a need to better identify boundaries between tissue and contrast agent-containing regions of an ultrasound image.

SUMMARY OF THE INVENTION

The method of the invention controls an ultrasound system to identify a boundary between a tissue region and a blood-filled region that lies within an ROI. A first embodiment of the method initially administers a contrast agent to the region of interest and then transmits a first ultrasound beam at a first power level into the ROI. Signal returns from the first beam are processed and stored as first digital signal values. Thereafter, a second ultrasound beam is transmitted at a second power level into the ROI and the signal returns therefrom are processed to derive second digital signal values which may then be used to identify a boundary between a blood filled cavity and tissue.

It has been determined that, under certain circumstances, a phase change of echo returns occurs at the boundary between tissue and blood-containing contrast agent. Detection of the phase change enables precise identification of the boundary, based upon the time segment in which the phase change is detected. Accordingly, time segment values of the first and second stored digital values are phase-compared to enable determination, by detection of a phase change, of a boundary location between the tissue region and the blood-filled region.

DETAILED DESCRIPTION OF THE PREFERRED EMBODIMENT

Figure 2:
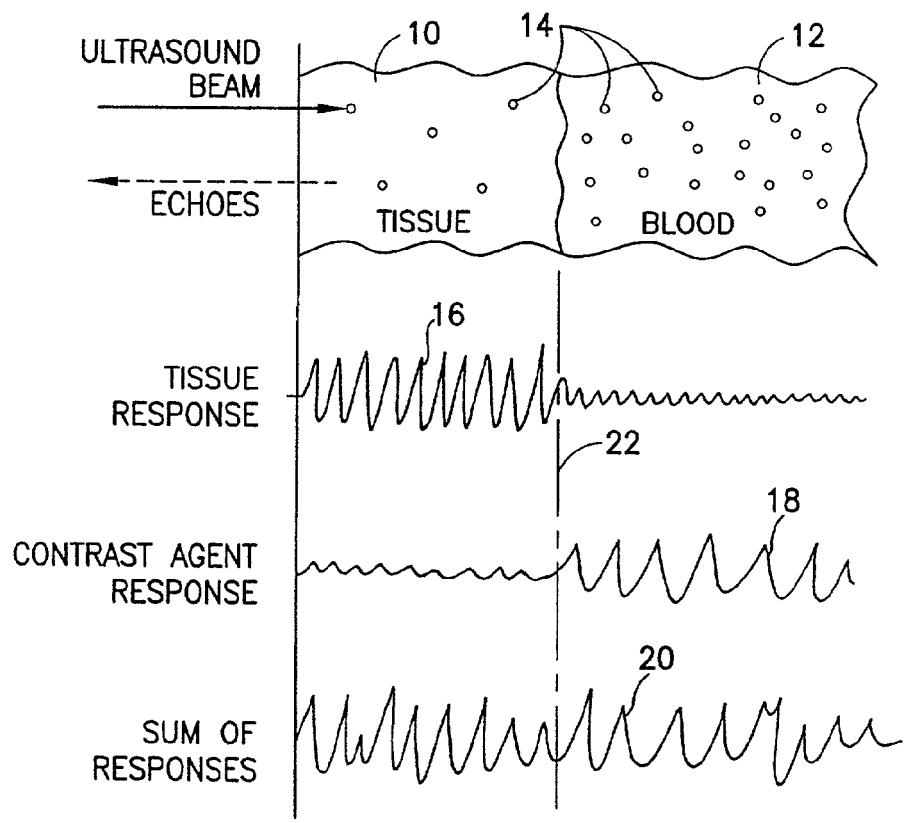
FIG. 2 comprises a series of schematics indicating the respective responses from tissue and blood-containing contrast agent and a combined response therefrom.

Referring to FIG. 2, the upper portion thereof illustrates an area of tissue 10 which borders a blood filled area 12, both of which contain contrast agent 14. Blood filled region 12 contains a higher concentration of contrast agent 14 than does tissue region 10. The respective echo response signals from regions 10 and 12 are shown by signals 16 and 18, respectively. The composite of the echo responses is shown by signal 20.

While there may be an amplitude difference between signal responses 16 and 18, the boundary between the respective signals is difficult to determine. It has been determined, however, that sum echo signal 20 exhibits a phase change at a position therein that is coincident with reflections from boundary 22 between tissue and blood-filled regions 10, 12. The reason for this phase change relationship can be better understood by referring to FIGS. 3a and 3b.

Figure 3A:
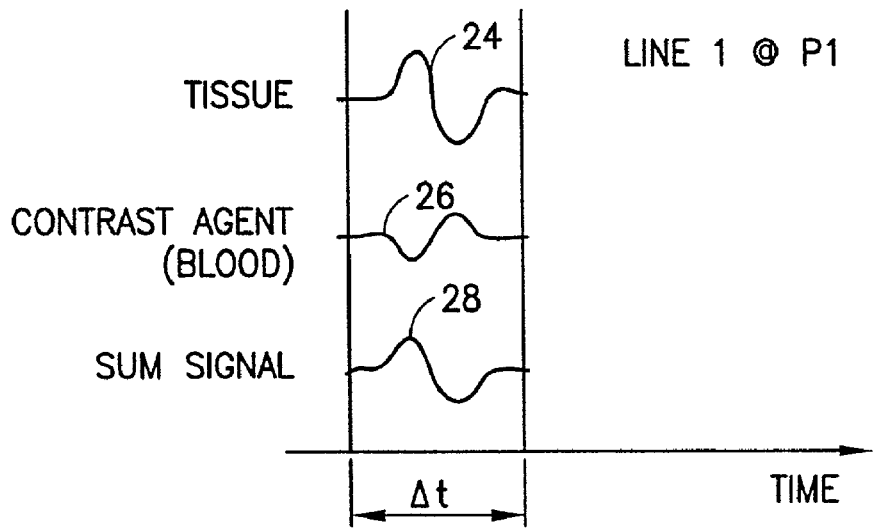
FIG. 3a illustrates the phase relationships of echo returns resulting from a single transmit event at a first low power level.

FIG. 3a illustrates signal returns resulting from a first transmit event (i.e., line 1) that is delivered at a power P1. Time segment delta t is selected from the echo response signals. The tissue echo response signal is shown at 24 and the contrast agent echo response signal at 26. Due to non-linearity of the response characteristic of signal echoes from contrast agent 14, the ultrasound echoes from tissue 10 and blood 12 vary widely in phase and in a non-deterministic manner.

Figure 1:
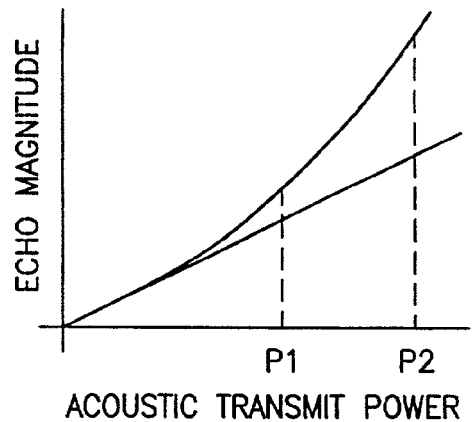
FIG. 1 is a plot of echo magnitude versus acoustic transmit power showing the response of both a contrast agent and tissue.

However, at a lower incident signal power level (e.g., P1), echo returns from tissue predominate—due to the density of the tissue and the fact that the nonlinear response increase of contrast agent is not significant at that power level. By contrast, at a higher incident signal power level (e.g., P2), the nonlinear increase in echo magnitude from contrast agent 14 causes it to dominate over the tissue echo response signals. Accordingly, if an echo signal 26 from contrast agent 14 is out-of-phase with an echo signal 24 from tissue 10 (which can randomly occur), at the higher power transmit level, the higher amplitude of echo signal 26 will cause the phase of echo signal 24 to be overridden and a phase reversal of the sum echo signal will be seen. This effect will not, however occur at the lower power level. Further, if power P1 is at a relatively low level (e.g., see FIG. 1), the amplitude of signal 26 is relatively low and sum signal 28, which is the addition of signals 24 and 26, is in-phase with tissue response signal 24 due to the predominance of signal 24. This condition (at power P1) will generally exist when time segment delta t captures a sum response signal that constitutes an echo signal from tissue region 10.

Figure 3B:
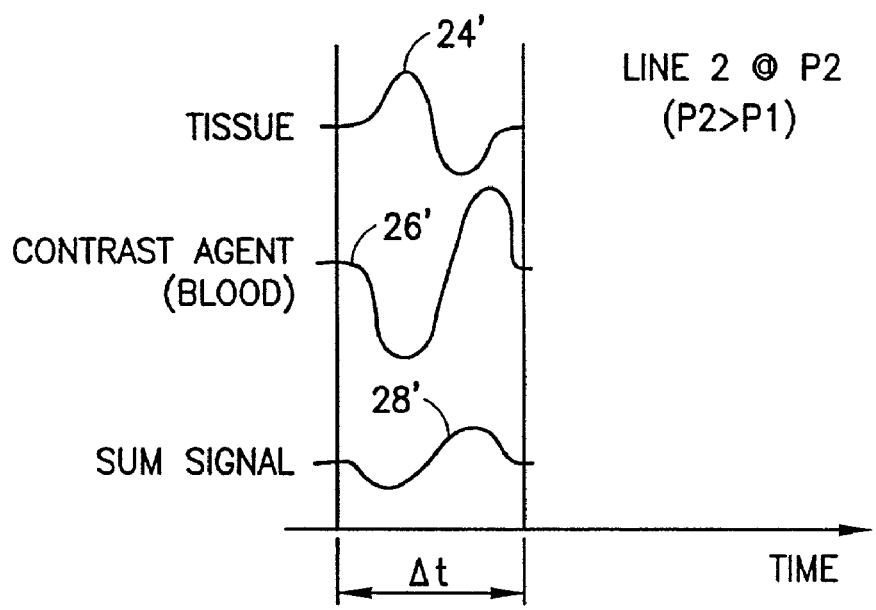
FIG. 3b illustrates the phase relationship of echo returns from a transmit event at a second higher power level.

FIG. 3b shows signal relationships when a second transmit event (line 2) is generated at a power level P2, where power level P2 is greater than power level P1. In this instance, due to the non-linear relationship of the response characteristic from contrast agent 14 (see FIG. 1), signal 26' evidences a substantially higher amplitude than signal 24' from tissue 10. Accordingly, sum signal 28' evidences a phase characteristic that is dominated by the contrast agent echo response signal 26' and, evidences an out-of-phase relationship with tissue echo response signal 24'.

The change in amplitude of signal 26' is due to the non-linear response characteristic of contrast agent 14 and is further enhanced when time segment delta t captures an echo response signal from the increased concentration of contrast agent 14 in blood 12. By correlating the time segment delta t (wherein a phase change from in-phase to out-of-phase occurs, as determined from sum signals 28 and 28' and tissue signals 24 and 24'), the location of boundary 22 between tissue 10 and blood 12 can be identified.

Note that since the effects discussed above occur on a random basis, if a change in phase occurs, it is saved as an indication of a picture element where a boundary point has been found. Over a plurality of transmit events, a number of phase change occurrences will probably be detected. Then, a "connect the dots" method can be used to fill in intervening picture elements where no phase change was detected.

Figure 4:
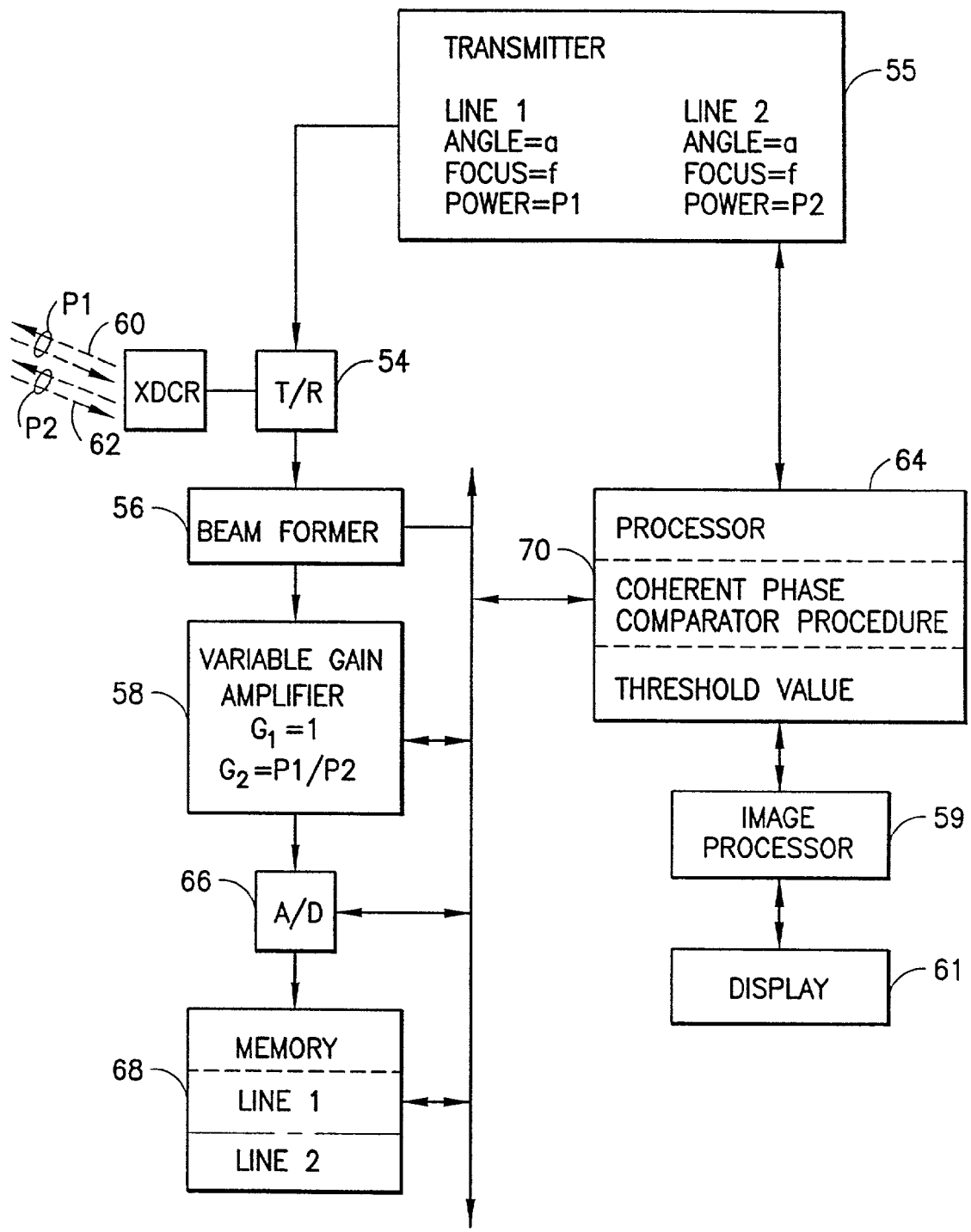
FIG. 4 illustrates a block diagram of a system adapted to carry out the method of the invention.

Turning now to FIG. 4, ultrasound system 50 includes a transducer 52 that is powered via a transmit/receive switch 54 from a transmitter 55. As will be hereafter understood, transmitter 55 is controlled by processor 64 to generate, sequentially, two ultrasound beams 60 and 62 at the same angle, using the same focal point, but at different power levels. Power level P1 of ultrasound beam 60 is less than the power level P2 of ultrasound beam 62.

Echo signals are received via transducer 52 and passed via transmit/receive switch 54 to a beamformer 56 of conventional design. The output of beamformer 56 is fed to a variable gain amplifier 58 that is, in turn, controlled by an input from processor 64. Prior to generation of beam 60, variable gain amplifier 58 is set to evidence a gain of 1 and prior to generation of beam 62, to a gain that is equal to P1/P2 to scale the second echo response signal to the first echo response signal. The "line" of echo signals derived from beam 60 are passed by variable gain amplifier 58 with a unitary gain. The output of variable gain amplifier 58, in that condition, includes both tissue response returns and contrast agent returns. The output of variable gain amplifier 58, when higher power ultrasound beam 62 is generated and an echo response signal is received, is dominated by the non-linear portions of the return signal when the echo signals are those returned from the blood filled region 12 (see FIG. 2).

Both the P1 and P2 echo return signals, in time sequence, are passed through an analog to digital converter 66 which transforms the respective outputs into a time series of digital values. The respective digital signal values are stored in memory 68 as line 1 and line 2, respectively. Thereafter, processor 64 initiates a coherent phase comparator procedure 70 which selects time segments of the line 1 and line 2 digital signal values in a manner to assure time "coherence" therebetween.

Coherent phase comparator procedure 70 then subtracts from the line 2 values (P2), the line 1 signal values (P1). Subtraction of these two values leaves a difference signal that exhibits a phase relationship that changes at boundary 22 and is either out-of phase or in-phase with the tissue echo return signal (see FIGS. 3a, 3b). If the signals are in-phase, it can be concluded that the signal is dominated by echo returns from either tissue or contrast agent and a boundary has not yet been reached. By contrast, if the difference signal evidences an out-of-phase relationship with the echo return signal, the boundary has been reached. The phase change occurs because the amplitude of the contrast agent echo return signal at the P2 power level experiences a significant increase at the increased power level. Thus the phase of the contrast agent echo return signal dominates at the higher P2 power level. Further, at boundary 22 the concentration of contrast agent changes markedly.

Accordingly, as coherent phase comparative procedure 70 steps along through the time segments of lines 1 and 2, the first time segment to show the phase change relationship indicates the time point at which the boundary between tissue and blood is detected. The time segment of the phase change signal is then related to the remaining signals of the ultrasound image, allowing the position of the boundary in the image to be determined. The resultant detected boundary can then be enhanced by, for example, assignment of a color value to the picture elements that define the boundary region.

Figure 5:
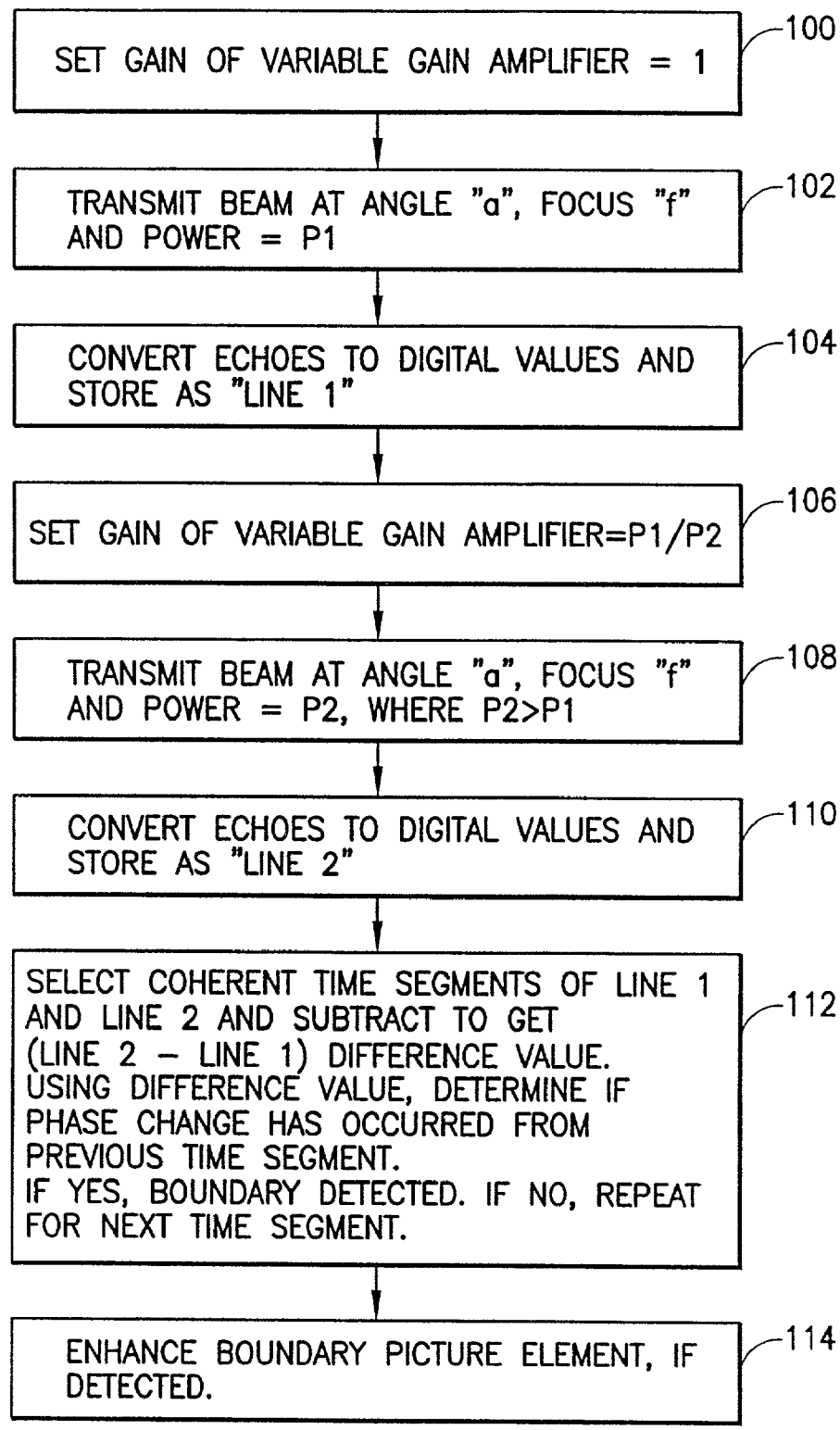
FIG. 5 is a flow diagram illustrating the method of the invention, as implemented by the system of FIG. 4.

Turning now to FIG. 5, the method of the invention will be described in conjunction with the flow diagram shown therein. Initially, variable gain amplifier 58 is set at unity gain (step 100). Thereafter, ultrasound beam 60 is caused to be transmitted at an angle "a" with a focus "f" and a power equal of P1 (step 102). The return signals are processed through variable gain amplifier 58, at the unitary gain setting. The output signals therefrom are converted to digital values and stored as "line 1" in memory 68 (step 104).

Next, the gain of variable gain amplifier 58 is set to the ratio of P1/P2 (step 106) and beam 62 is transmitted at the same angle and focus as beam 60, but with an increased power P2 (step 108). The return echoes are processed by variable gain amplifier 58, using the gain setting of P1/P2. This gain setting scales the second response signal to the first response signal and the resulting scaled signal is converted to digital values and stored as "line 2" (step 110).

At this stage, coherent phase comparator procedure 70 selects succeeding time coherent segments of data from the line 1 and line 2 storage areas in memory 68 and then compares their respective phases (step 112). If no phase change is detected from a time segment signal in a previous time segment, no boundary has been reached. By contrast, if a phase change is detected, a boundary has been found.

As an alternative embodiment, the line 1 and line 2 signals may be subtracted to derive (line 2–line 1). The difference value (line 2–line 1) is then subjected to a threshold and if the difference value exceeds the threshold, the phases of the line 1 and (line 1–line 2) time segment signals are then compared (step 112). Otherwise, the procedure repeats for a next time segment.

Thereafter, processor 64 (see FIG. 4) outputs the resulting boundary data to image processing module 59 which superimposes a signal enhancement on the resulting ultrasound image to better identify the boundary region (step 114). The enhanced signals are then fed to display 61 (see FIG. 4) for review by the user.

As indicated above, introduction of contrast agents can be used to improve the delineation of blood-filled structures, especially in patients that would otherwise have poor diagnostic quality images. In images obtained without contrast agents, the tissue structures normally are presented as brighter intensities, while blood-filled cavities, because of their relative lack of returned echo signals, appear darker than the tissues surrounding them. However, when contrast agents are introduced, because of the greater volumetric concentration of contrast agents in the cavities than in the tissues, the cavities subsequently appear with brighter intensities than the surrounding tissues.

In the prior art (see U.S. Pat. No. 5,195,521 to Melton et al.), a thresholding operation is applied to the image intensity data. The image samples that are of greater intensity than a threshold are classified as tissue and the image samples that are of lesser intensity than a threshold are classified as blood. A boundary is indicated where the areas of image samples classified as tissue meet areas of image samples classified as blood. Newer contrast detection techniques (see U.S. Pat. No. 5,577,505) serve to further increase the cavity-to-tissue intensity ratio when contrast agents are used. Further, the multi-power level procedure described herein provides an even better ratio of intensities as between blood pools containing contrast agent and tissue.

Accordingly, it has been determined that an improved method for defining tissue boundaries can be implemented when contrast agents are introduced into circulation. As the relative intensity relationship between tissue and the cavity areas is reversed, with blood pools being brighter than tissue (as described above), a threshold detection action can be used to classify a boundary between tissue and a blood filled cavity. More particularly, areas are classified as cavity where the image intensity is greater than a threshold, and areas are classified as tissue where the image intensity is less than a threshold. The regions where the classification changes are indicative of the position of a boundary.

It should be understood that the foregoing description is only illustrative of the invention. Various alternatives and modifications can be devised by those skilled in the art without departing from the invention. For example, (i) one or more frequency components of one of the ultrasound beams may be modulated in phase with respect to the other ultrasound beam; (ii) the first and second ultrasound beams may be transmitted in phase coherence when considering a reference time; or (iii) the ultrasound beams may be transmitted in phase opposition when considering a reference time. In each case, the summed phase relationship of echoes that result from the beams will enable the determination of a boundary picture element. Further, while each of the procedures required to operate the invention have been described as loaded into memory, they may be stored on a memory device (e.g. a magnetic floppy disk) and loaded on an as-needed basis. Accordingly, the present invention is intended to embrace all such alternatives, modifications and variances which fall within the scope of the appended claims.

What is claimed is:

1. An ultrasound method for determining boundaries of a fluid-filled cavity, comprising the steps of:
   introducing a contrast agent into a fluid-filled cavity within a body; and
   imaging the fluid-filled cavity and surrounding tissue such that an image is created where the contrast agent in the fluid-filled cavity is represented in brighter intensities than is said surrounding tissue;
   applying a threshold value to pixel data values comprising regions of the image;
   classifying brighter areas of the image as representing the fluid-filled cavity and darker areas of the image as representing surrounding tissue, wherein the classifying includes detecting pixels comprising the fluid/tissue cavity boundary utilizing phase comparison means.

2. The method as recited in claim 1, comprising the further step of:
   determining a boundary between said fluid-filled cavity and said surrounding tissue by detecting a region where brighter areas of the fluid-filled cavity adjoin darker areas of said surrounding tissue.

3. The method as recited in claim 2, comprising the further step of:
   performing real time calculations employing said determined boundary.

4. A memory media including instructions for controlling an ultrasound system to determine boundaries of a fluid-filled cavity into which a contrast agent has been introduced, comprising
   a) means for controlling said ultrasound system to image the fluid-filled cavity and surrounding tissue such that an image is created where the contrast agent in the fluid-filled cavity is represented in brighter intensities than is said surrounding tissue;
   b) means for controlling said ultrasound system to apply a threshold value to pixel data values comprising regions of the image; and
   c) means for controlling said ultrasound system to classify brighter areas of the image as representing the fluid-filled cavity and darker areas of the image as representing surrounding tissue, wherein pixels comprising a fluid-tissue boundary are identified utilizing phase comparator means.

5. The memory media as recited in claim 4, further comprising:
   d) means for controlling said ultrasound system to determine a boundary between said fluid-filled cavity and said surrounding tissue by detecting of a region where brighter areas of the fluid-filled cavity adjoin darker areas of said surrounding tissue.

6. The memory media as recited in claim 5, further comprising:
   d) means for controlling said ultrasound system to perform real time calculations employing said determined boundary.

* * * * *